US008307824B2

(12) United States Patent
Cuevas et al.

(10) Patent No.: US 8,307,824 B2
(45) Date of Patent: Nov. 13, 2012

(54) METHOD OF PERFORMING A TRACHEOSTOMY

(75) Inventors: Brian J. Cuevas, Cumming, GA (US); Michael Sleva, Atlanta, GA (US); Joe Cesa, Cumming, GA (US); Marjory Greenhalgh, Decatur, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1166 days.

(21) Appl. No.: 12/147,873

(22) Filed: Jun. 27, 2008

(65) Prior Publication Data
US 2009/0320833 A1    Dec. 31, 2009

(51) Int. Cl.
*A61M 16/00* (2006.01)

(52) U.S. Cl. ......... 128/200.26; 128/200.24; 128/207.14; 128/207.29

(58) Field of Classification Search ............. 128/200.24, 128/200.26, 207.14–207.18, 207.29
See application file for complete search history.

(56) References Cited

U.S. PATENT DOCUMENTS

| 460,987 A | 10/1891 | Olivieri |
| 2,865,374 A | 12/1958 | Brown et al. |
| 3,511,243 A * | 5/1970 | Toy .......................... 128/207.29 |
| 4,211,234 A * | 7/1980 | Fisher ..................... 128/200.26 |
| 4,246,897 A | 1/1981 | Muto |
| 4,364,391 A | 12/1982 | Toye |
| 4,471,778 A | 9/1984 | Toye |
| 4,488,545 A | 12/1984 | Shen |
| 4,677,978 A | 7/1987 | Melker |
| 4,869,718 A | 9/1989 | Brader |
| 4,898,163 A | 2/1990 | George |
| 4,978,334 A | 12/1990 | Toye et al. |
| 5,058,580 A | 10/1991 | Hazard |
| 5,090,408 A | 2/1992 | Spofford et al. |
| RE34,086 E | 10/1992 | George |
| 5,156,601 A | 10/1992 | Lorenz et al. |
| 5,181,509 A | 1/1993 | Spofford et al. |
| 5,186,168 A | 2/1993 | Spofford et al. |
| 5,217,005 A | 6/1993 | Weinstein |

(Continued)

FOREIGN PATENT DOCUMENTS
AT    146305    6/1936
(Continued)

OTHER PUBLICATIONS

EM000022306. 0001 Design, Aug. 19, 2003.

*Primary Examiner* — Loan Thanh
*Assistant Examiner* — Kathryn D Sheikh
(74) *Attorney, Agent, or Firm* — James B. Robinson

(57) ABSTRACT

There is provided a method for performing a tracheotomy. In this method a tracheostomy dilator has a body and a tip which are detachably attached. The tip has a proximal inner portion which is within the body while the tip is attached to the body. The dilator is inserted into the trachea and used to dilate an opening. After the trachea has been dilated, the body may be detached and removed from the tip, the tip remaining partially in the trachea. A dilator loading catheter installed within a tracheostomy tube may be mated with the tip and the tip, loading catheter and tracheostomy tube moved into the trachea. After the tracheostomy tube is installed, the tip and loading catheter may be withdrawn through the tracheostomy tube and the tracheostomy tube placed in service.

4 Claims, 18 Drawing Sheets

U.S. PATENT DOCUMENTS

| | | | |
|---|---|---|---|
| 5,258,421 A | 11/1993 | Lorenz et al. | |
| 5,297,546 A | 3/1994 | Spofford et al. | |
| 5,420,197 A | 5/1995 | Lorenz et al. | |
| 5,653,230 A | 8/1997 | Ciaglia et al. | |
| 5,690,669 A | 11/1997 | Sauer et al. | |
| 6,054,504 A | 4/2000 | Dalla Riva Toma | |
| 6,109,264 A | 8/2000 | Sauer | |
| 6,298,851 B1 | 10/2001 | Parota et al. | |
| 6,382,209 B1 | 5/2002 | Toye | |
| 6,588,426 B2 * | 7/2003 | Linderoth | 128/207.14 |
| 6,637,435 B2 | 10/2003 | Ciaglia et al. | |
| D485,358 S | 1/2004 | Woo | |
| 6,706,017 B1 | 3/2004 | Dulguerov | |
| 6,939,318 B2 * | 9/2005 | Stenzel | 604/60 |
| 7,036,510 B2 | 5/2006 | Zgoda et al. | |
| 7,341,061 B2 * | 3/2008 | Wood | 128/207.29 |
| 7,945,307 B2 * | 5/2011 | Lubock et al. | 600/414 |
| 2002/0066453 A1 * | 6/2002 | Ciaglia et al. | 128/207.29 |
| 2003/0114871 A1 * | 6/2003 | Turnbull | 606/167 |
| 2004/0049222 A1 | 3/2004 | Schaeffer et al. | |
| 2004/0087991 A1 | 5/2004 | Woo | |
| 2004/0098013 A1 | 5/2004 | Ciaglia et al. | |
| 2004/0154623 A1 | 8/2004 | Schaeffer et al. | |
| 2005/0183729 A1 | 8/2005 | Fischer, Jr. | |
| 2006/0081260 A1 | 4/2006 | Eels et al. | |
| 2006/0100657 A2 | 5/2006 | Ciaglia et al. | |
| 2006/0124134 A1 | 6/2006 | Wood | |
| 2007/0227543 A1 | 10/2007 | Peichel | |
| 2009/0320834 A1 * | 12/2009 | Cuevas et al. | 128/200.26 |
| 2009/0320854 A1 * | 12/2009 | Cuevas et al. | 128/207.29 |
| 2010/0300451 A1 * | 12/2010 | Griffith et al. | 128/207.29 |
| 2011/0265797 A1 * | 11/2011 | Waldron | 128/207.14 |
| 2011/0290245 A1 * | 12/2011 | Cuevas et al. | 128/200.26 |

FOREIGN PATENT DOCUMENTS

| | | |
|---|---|---|
| DE | 3015593 A1 | 10/1981 |
| DE | 10065604 A1 | 7/2001 |
| EP | 0371752 A1 | 6/1990 |
| EP | 1099451 A2 | 5/2001 |
| EP | 1281414 B1 | 9/2004 |
| GB | 2377382 | 1/2003 |
| GB | 2394669 | 5/2004 |
| JP | 3173577 A | 7/1991 |
| JP | 200595401 | 4/2005 |
| WO | WO 95/32017 | 11/1995 |
| WO | WO 2006/008602 | 1/2006 |
| WO | WO 2006/087032 | 8/2006 |
| WO | WO 2006/087512 | 8/2006 |
| WO | WO 2006/120077 | 11/2006 |
| WO | WO 2007/000159 | 1/2007 |
| WO | WO 2008/009943 | 1/2008 |
| WO | WO 2008/034872 | 3/2008 |

* cited by examiner

METHOD OF PERFORMING A TRACHEOSTOMY

Ventilators or respirators are used for mechanical ventilation of the lungs of a patient in a medical setting. The ventilator unit is connected to a hose set; the ventilation tubing or tubing circuit, delivering the ventilation gas to the patient. At the patient end, the ventilation tubing is typically connected to a tracheal ventilation catheter or tube, granting direct and secure access to the lower airways of a patient. Tracheal catheters are equipped with an inflated sealing balloon element, or "cuff", creating a seal between the tracheal wall and tracheal ventilation tube shaft, permitting positive pressure ventilation of the lungs.

One type of tracheal catheter, an endotracheal tube (ET tube), inserted through the mouth, is generally used for a number of days before a decision is made to switch a patient to a tracheostomy tube, inserted directly into the trachea through a stoma in the tracheal wall. Endotracheal tubes have been linked in some studies to an increased rate of ventilator acquired pneumonia (VAP) and so tracheostomy operations are becoming increasingly common and are being performed earlier in the patient's hospital stay in order to reduce the occurrence of VAP.

A tracheostomy procedure involves making a small horizontal incision in the skin of the neck to grant access to the trachea. Because of the uniquely flexible and elastic nature of the trachea, it has been found that healing is much faster if only a small hole is made in the tracheal wall and the hole dilated, rather than cutting the tracheal wall. After the skin incision, a hemostat or other implement may be used to separate the subcutaneous tissues to gain access to the trachea, and digital palpation is used to locate the tracheal rings. A bronchoscope is usually inserted into the ET tube and the tube withdrawn from the trachea until the light of the bronchoscope transdermally illuminates the site of the incision. A sheathed needle is used to puncture the tracheal wall, usually between the second and third tracheal rings. The needle is removed with the sheath remaining, a flexible guide wire (also called a J-wire) is inserted in the place of the needle and the sheath is removed. The bronchoscope is used for viewing the procedure from within the trachea in order to avoid damage to the tracheal wall. A small (e.g. 14 French) introducer dilator is introduced over the guide wire to perform an initial dilation of the tracheal wall, and then removed. A smaller (e.g. 8 French) guiding catheter is then introduced over the guide wire. (Note, French is a measure of circumference based on the theory that non-round tubes of the same circumference will fit into the same incision. One French is approximately 0.33 mm or 0.013 inch).

After the guiding catheter is introduced, a first dilator such as the Cook Medical Inc. Blue Rhino® dilator (see also U.S. Pat. No. 6,637,435), is placed over the guide wire and the guiding catheter and first dilator are advanced into the trachea through the tracheal wall as a unit to perform the dilation. Cook Medical recommends a slight over-dilation of the tracheal wall in order to make the placement of the tracheostomy tube easier. After dilation, the first dilator is removed and the tracheostomy tube (with cannula removed) is introduced over the guide catheter using a second, loading dilator that fits just inside the trachostomy tube and protrudes about 2 cm beyond the distal end of the tracheostomy tube. The guide catheter, second dilator and tracheostomy tube are advanced into the trachea through the tracheal wall as a unit. Once the tracheostomy tube is at the proper depth, the second dilator, guide catheter and guide wire are removed through the tracheostomy tube, the inner cannula inserted into the tracheostomy tube and the tube connected to the ventilator.

As can be understood from the above description, the current state of the art for tracheostomy involves numerous steps and the insertion and removal of a number of components before the successful completion of the procedure. For most of this time, the patient is disconnected from the ventilator and is therefore, not breathing. In addition, the large number of parts used in current tracheostomy kits increases the likelihood that an item may be accidentally rendered unsterile and be unable to be used. In such cases, the patient must be re-intubated with an ET tube. Even if the procedure proceeds uneventfully, however, the amount of time the patient is not breathing is significant; on the order of 7 minutes or more. This is clearly a significant event, especially for a patient who is, most likely, not in optimal physical condition.

There remains a need for a procedure that can more quickly and safely allow for the successful placement of a tracheostomy tube.

SUMMARY OF THE INVENTION

There is provided a method for performing a tracheostomy using a novel dilator, dilator loading catheter and tracheostomy tube In this method a tracheostomy dilator has a body and a tip which are detachably attached. The dilator is inserted into the trachea and used to dilate an opening. After the trachea has been dilated, the body may be detached and removed from the tip, the tip remaining partially in the trachea. A dilator loading catheter installed within a tracheostomy tube may be mated with the dilator tip and the tip, loading catheter and tracheostomy tube moved into the trachea. After the tracheostomy tube is inserted to the proper point, the dilator tip and loading catheter may be withdrawn through the tracheostomy tube and the tracheostomy tube placed in service.

DETAILED DESCRIPTION OF THE INVENTION

Tracheostomy is a lifesaving procedure to allow a patient to be ventilated directly through the trachea. Tracheostomy is also believed by many to prevent or retard the onset of ventilator acquired pneumonia (VAP). This lifesaving procedure, unfortunately, is relatively time consuming and current technology requires a large number of steps and pieces of equipment that must remain sterile and functioning properly in order to arrive at a successful conclusion.

Figure 1:
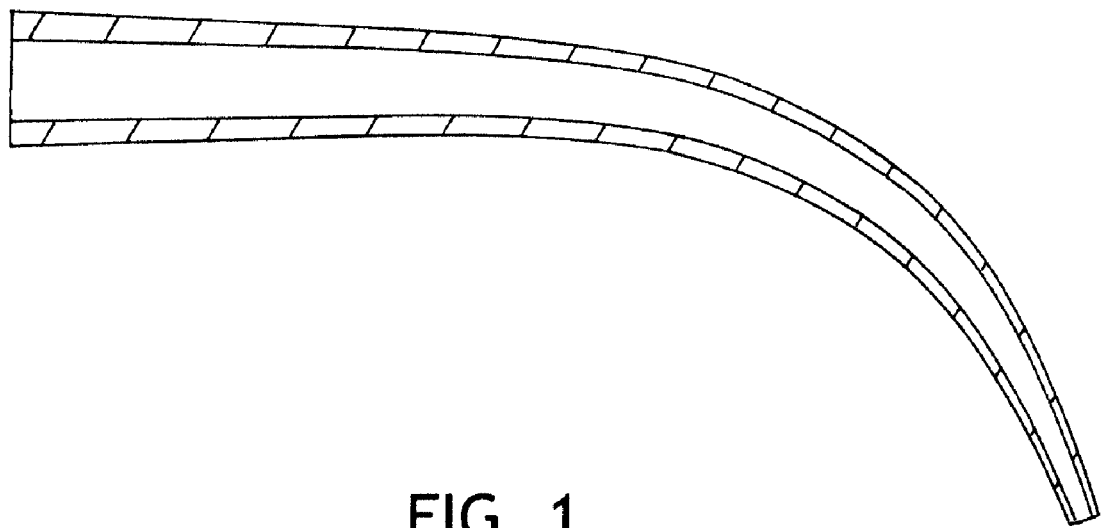
FIG. 1 is a drawing of the prior art Blue Rhino® dilator.

Dilators are instruments or substances for enlarging a canal, cavity, blood vessel or opening, according to the American Heritage Stedman's Medical dictionary 2001. FIG. 1 is a drawing of the prior art dilator from Cook Medical Inc. known as the Blue Rhino® dilator (see also U.S. Pat. No. 6,637,435). This patent describes a one piece dilator having a generally linear shaft and a short distal tip portion with a curved tapered portion in between.

The tracheostomy procedure may be greatly improved using the method described in the Summary above. The method reduces the number of steps used relative to the current state of the art procedure described in the introduction. The method uses a dilator that replaces both the first and second dilators and a dilator loading catheter and so provides fewer steps in the procedure, saving time and reducing risk to the patient.

Figure 2:
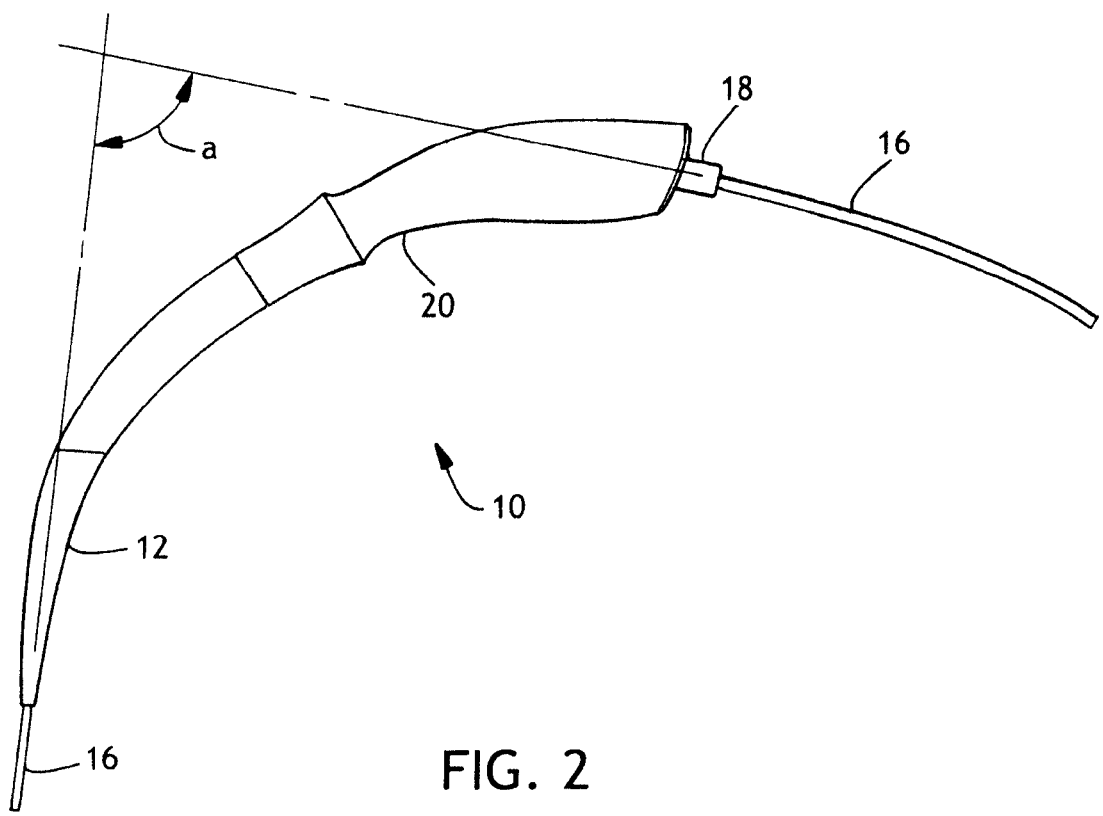
FIG. 2 is a drawing of the easy grip tapered dilator.
Figure 3:
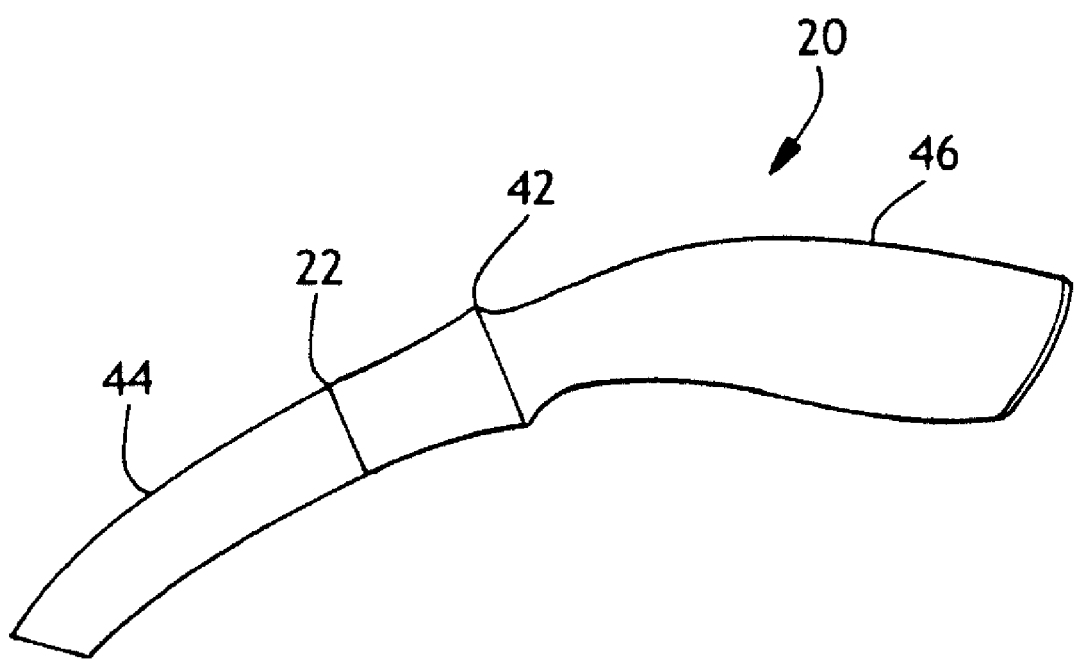
FIG. 3 is a drawing of the body or handle portion of the easy grip tapered dilator.
Figure 4:
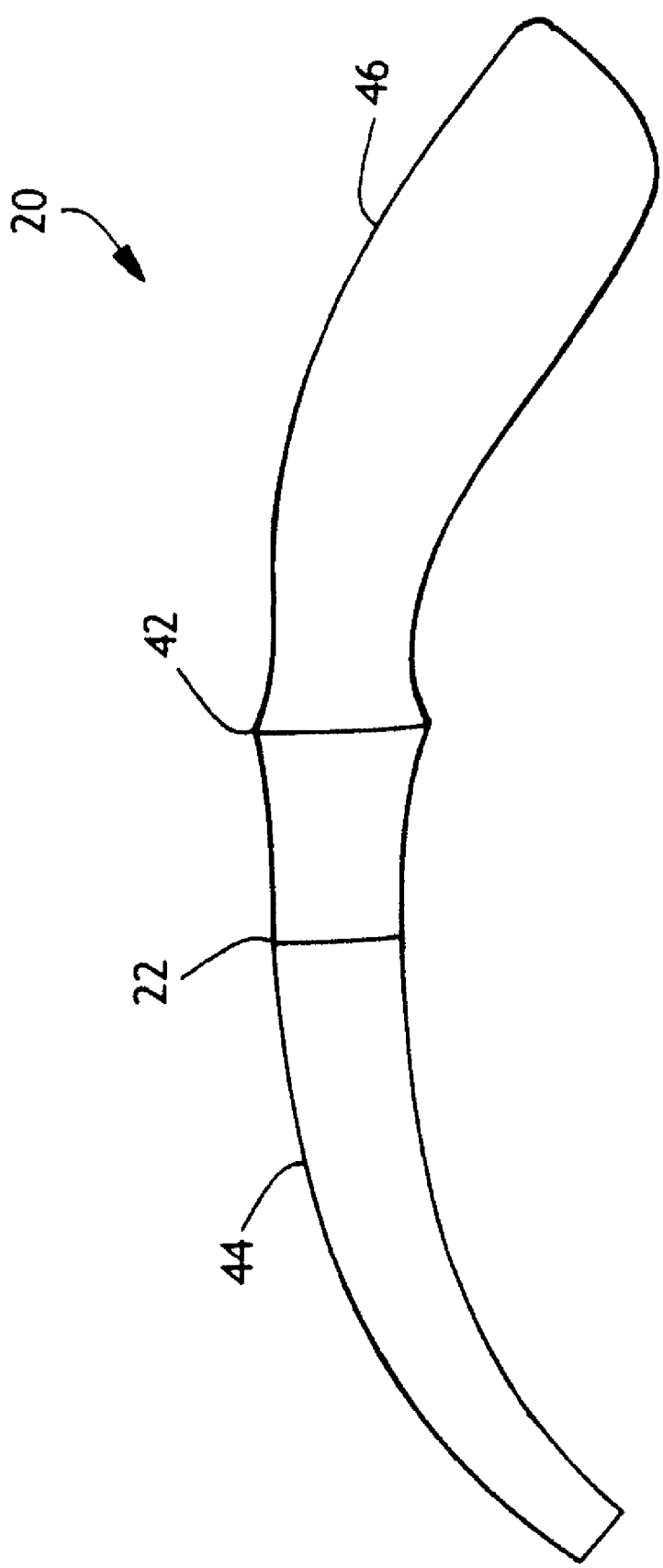
FIG. 4 is a drawing of an alternate embodiment of the body or handle portion of the easy grip tapered dilator.
Figure 5:
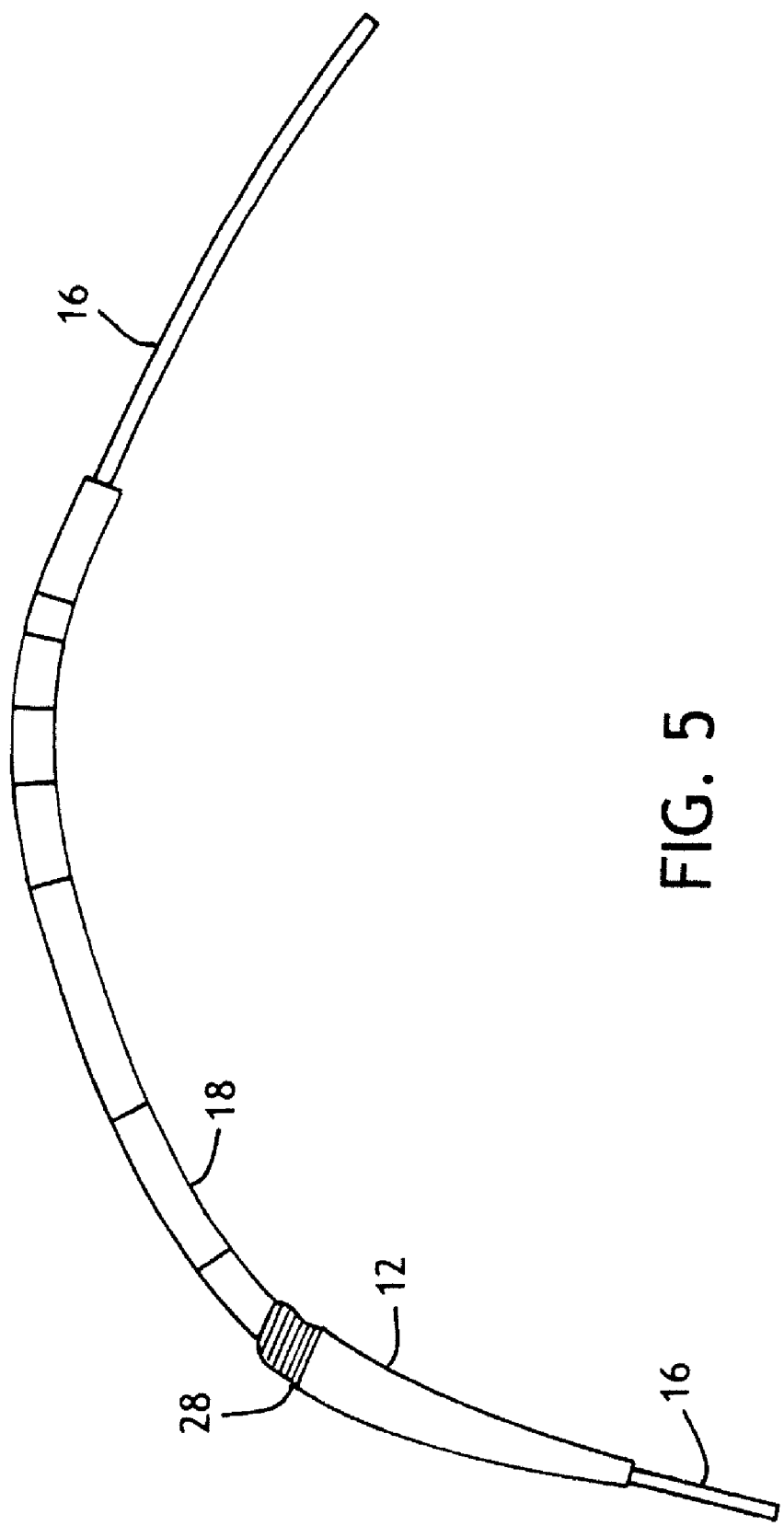
FIG. 5 is a drawing of the tip and inner portion of the easy grip tapered dilator.
Figure 6:
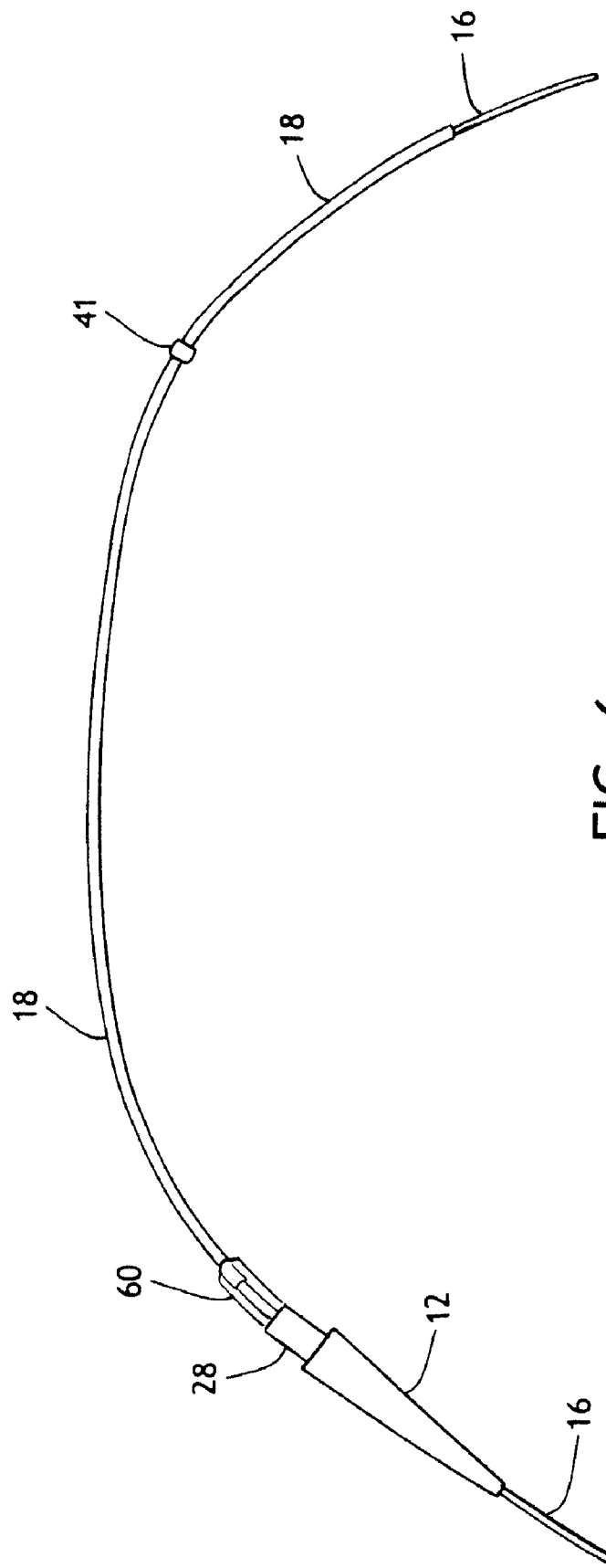
FIG. 6 is a drawing of an alternate embodiment of the tip and inner portion of the easy grip tapered dilator.

Turning to the Figures, one embodiment of the suitable dilator 10 has a body 20 and a distal tip 12 (FIG. 2) with an inner portion 18. A suitable dilator 10 has at least two parts or pieces wherein the tip 12 is detachably attached to the body 20. The body 20 is shown in FIG. 3 and has a marking line 22 or alternatively a ridge where the diameter is approximately 42 French which serves as a depth marking or insertion stopping point for the dilation procedure. An alternative embodiment of the body 10 to be used with the tip 12 embodiment of FIG. 6 is shown in FIG. 4. The body 20 has a distal portion 44 and a handle portion 46. The body is sized such that the inner portion 18 of the tip 12 can pass through it.

The distal tip 12 meets the body 20 at the proximal end 28 of the tip 12 (FIG. 4). The tip 12 has an proximal inner portion 18 that is surrounded by and passes through the dilator body 20 when the suitable dilator 10 is comprised of the tip 12 and body 20 connected together. The tip 12 has a cannula sized to accommodate a guiding catheter 14 (not shown) over the J-wire 16 so that the J-wire 16 may pass within the inner portion 18, into the tip 12 and exit the distal end of the tip 12 as shown in FIG. 4.

Figure 7:
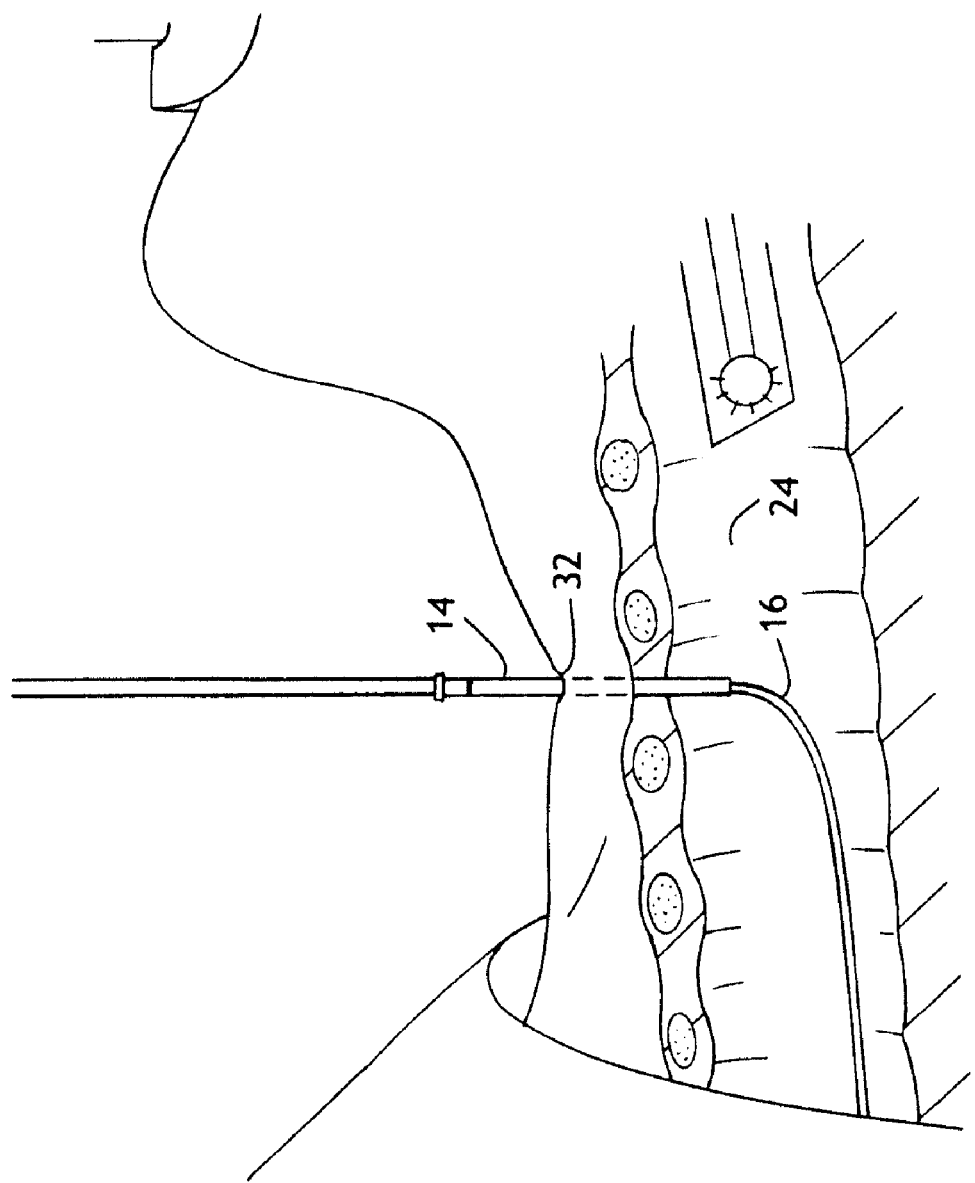
FIG. 7 is a drawing of the position of a guiding catheter being introduced over a J-wire in the trachea after initial dilation.
Figure 8:
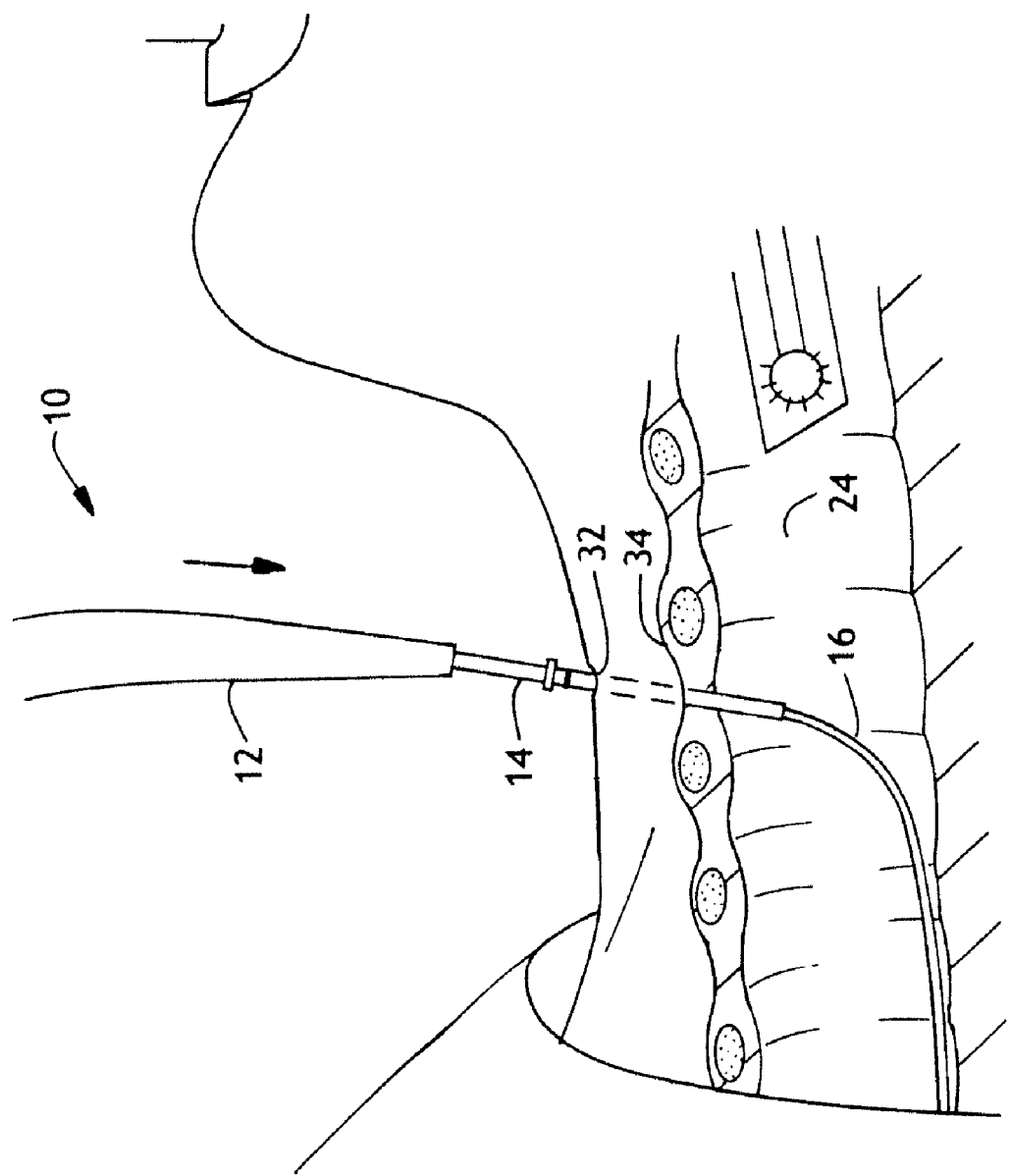
FIG. 8 is a drawing of the tip of the dilator being slipped over the guiding catheter through which runs the J-wire.
Figure 9:
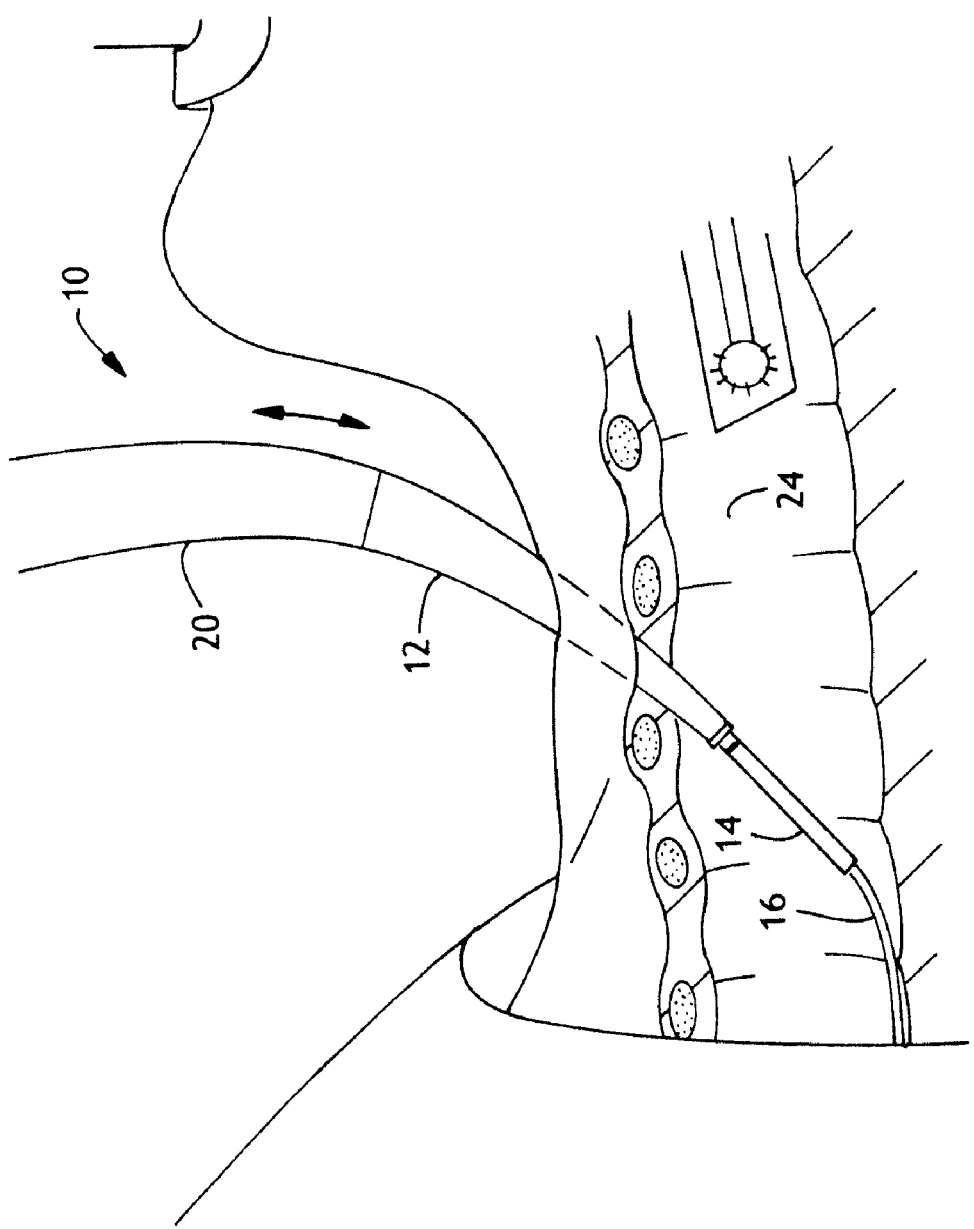
FIG. 9 is a drawing of the device, guiding catheter and J-wire being moved into the trachea through the tracheal wall
Figure 10:
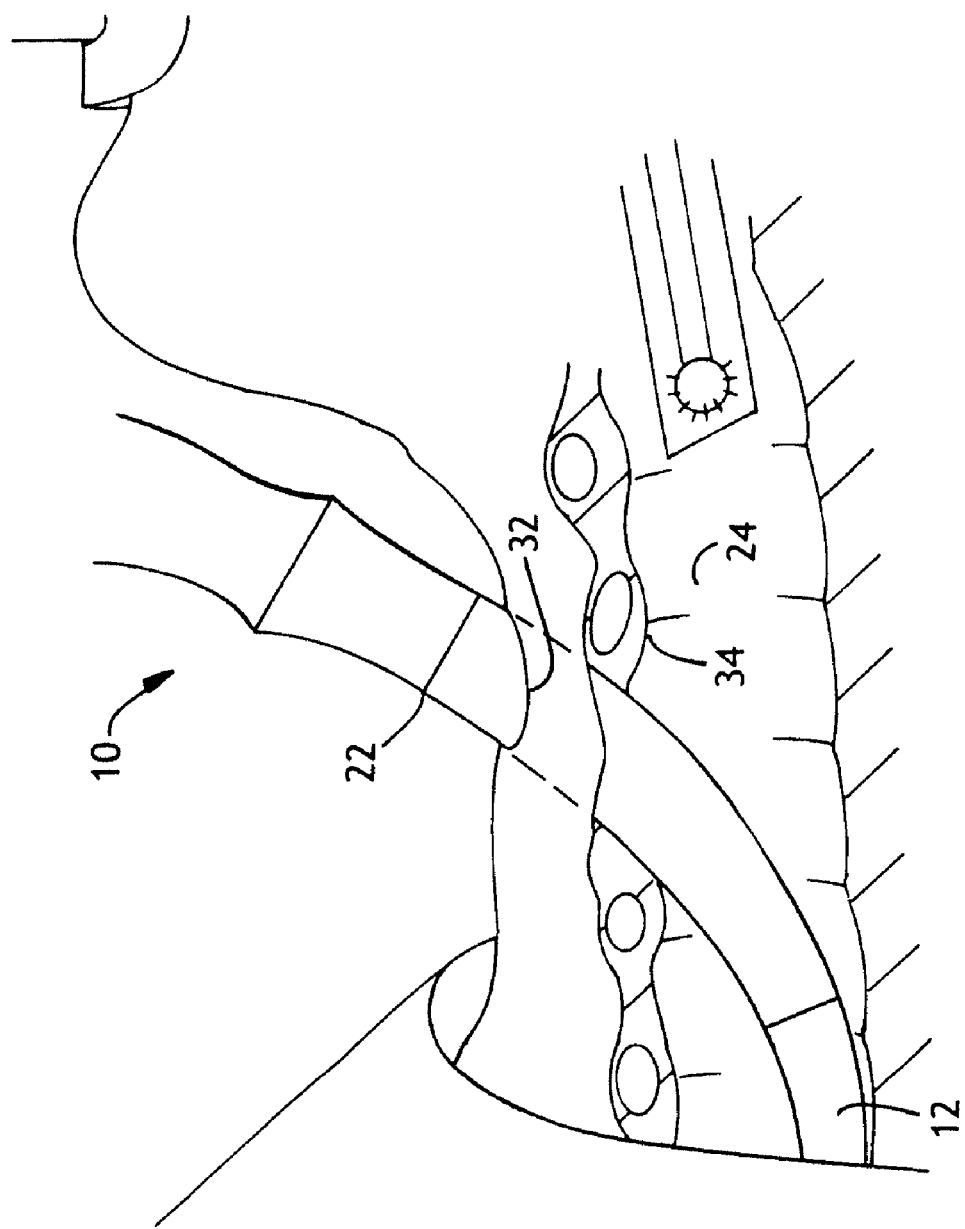
FIG. 10 is a drawing of the dilator having been inserted into the trachea through the tracheal wall to the point where the "stop" mark or insertion depth gauge, meets the incision.

As described above, once the J-wire 16 is inserted into the trachea 24 through the incision 32 and tracheal wall 34, a guiding catheter 14 is introduced over the J-wire 16 (FIG. 7). In the tracheostomy procedure using the suitable dilator 10, the tip 12 of the dilator 10 is slipped over the guiding catheter 14 through which runs the J-wire 16 (FIG. 8). It is also possible to produce the tip 12 of the dilator 10 such that the tip 12 incorporates the guiding catheter, thus removing the need for a separate guiding catheter (FIG. 6). The dilator 10, guiding catheter 14 and J-wire 16 are then moved into the trachea 24 through the tracheal wall 34 until the marking line 22 of the dilator 10, which serves as a "stop" mark or depth gauge, meets the incision 32 (FIGS. 9 and 10 sequentially). The actual procedure of dilation of the tracheal wall usually involves the repeated incremental insertion and removal of the dilator 10. This procedure may be made easier for the medical provider and less traumatic for the patient by the application of a lubricious coating to the dilator 10. The coating can reduce friction and drag on the J-wire 16 and also reduce trauma to the area of the incision 32 and the tracheal wall 34. This coating is described in more detail below.

Figure 11:
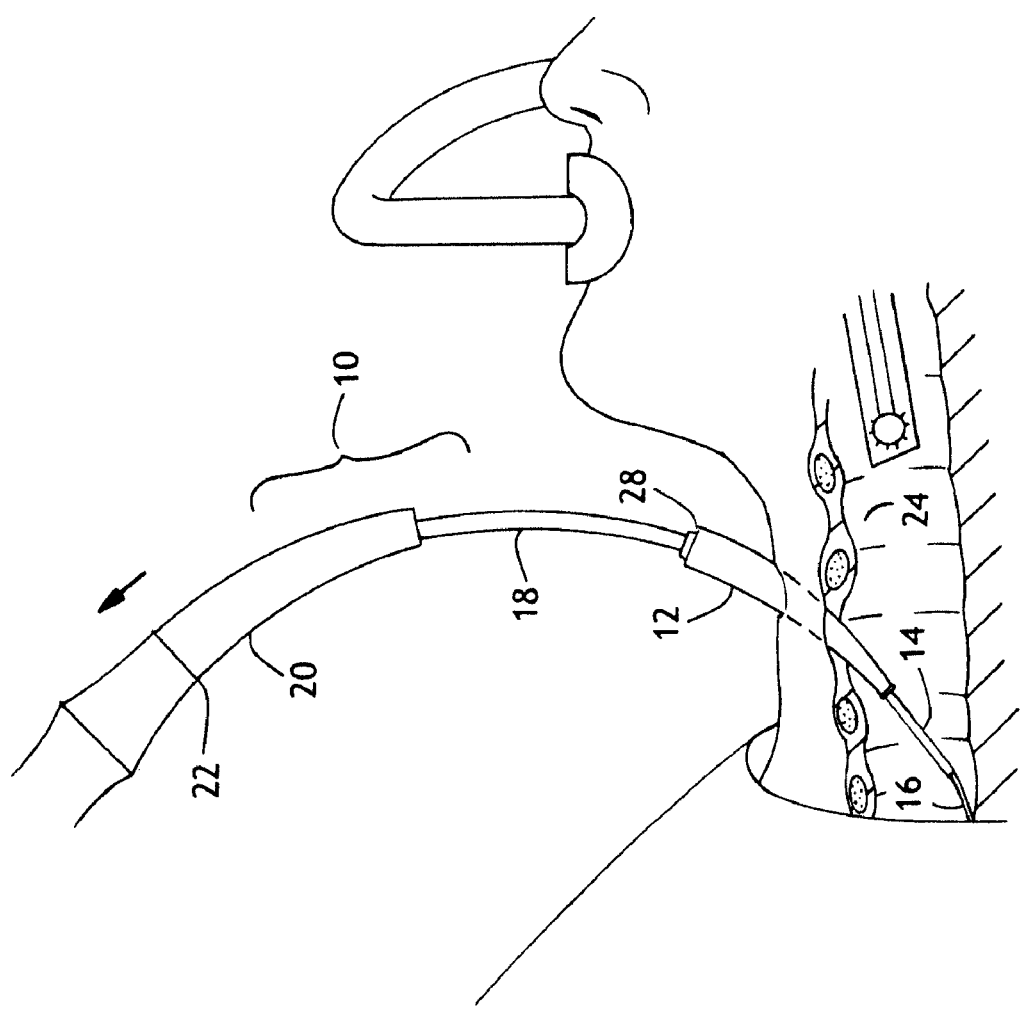
FIG. 11 is a drawing of the dilator body being removed as indicated by the arrow, leaving the tip, guiding catheter and J-wire.
Figure 12:
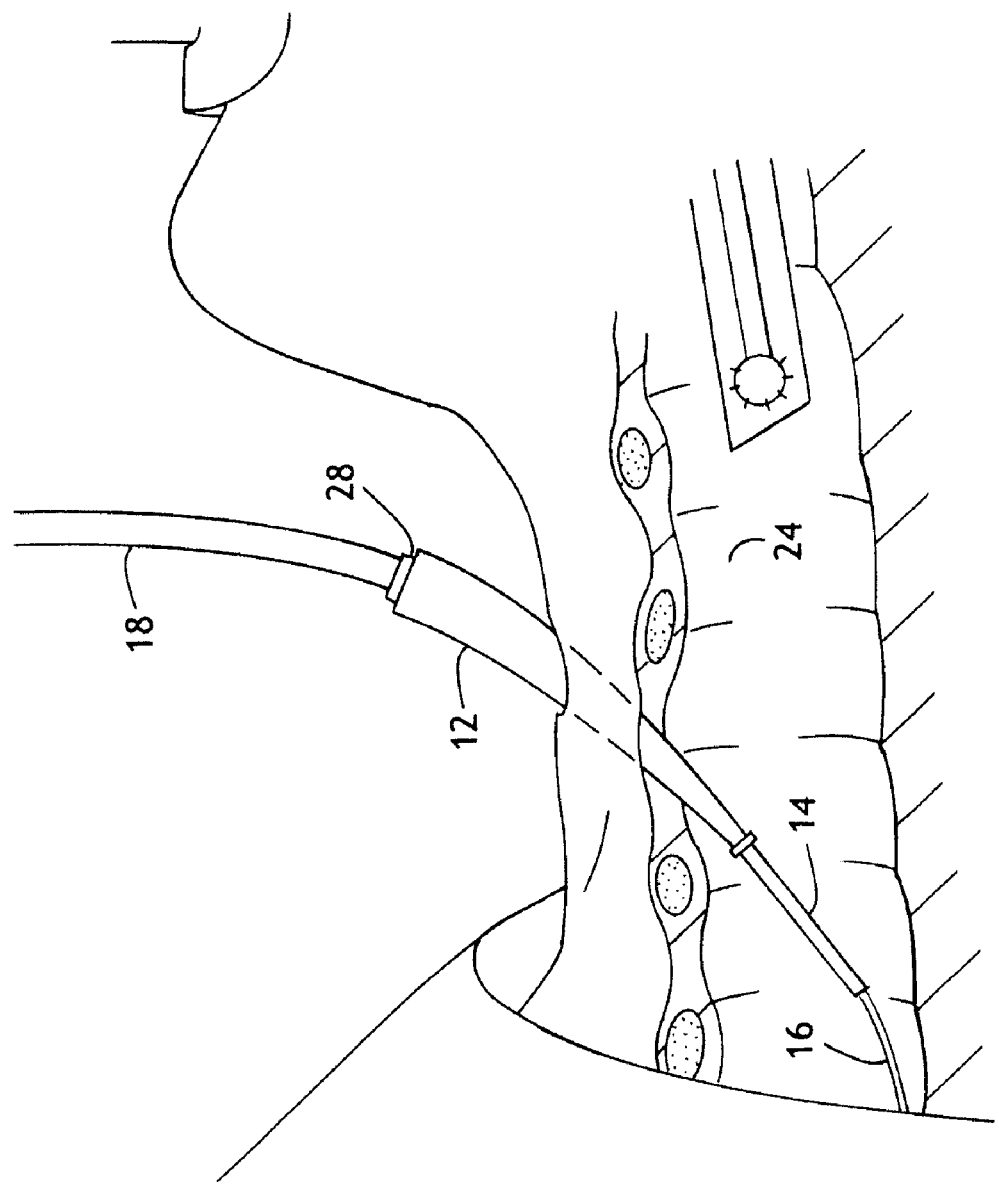
FIG. 12 is a drawing of the dilator tip, guiding catheter and J-wire in place in the trachea after removal of the dilator body.

Once the trachea 24 is satisfactorily dilated, the dilator 10 may be partially removed from the trachea 24, leaving the tip 12 partially, e.g., about halfway, into the trachea 24. Note that this view is essentially the same as FIG. 9 but occurs after the trachea 24 has been dilated. The dilator body 20 may then be removed as indicated by the arrow in FIG. 11, leaving the tip 12, guiding catheter 14 and J-wire 16 in place (FIG. 12). The inner portion 18 of the tip 12 is also visible in FIG. 12.

Figure 17:
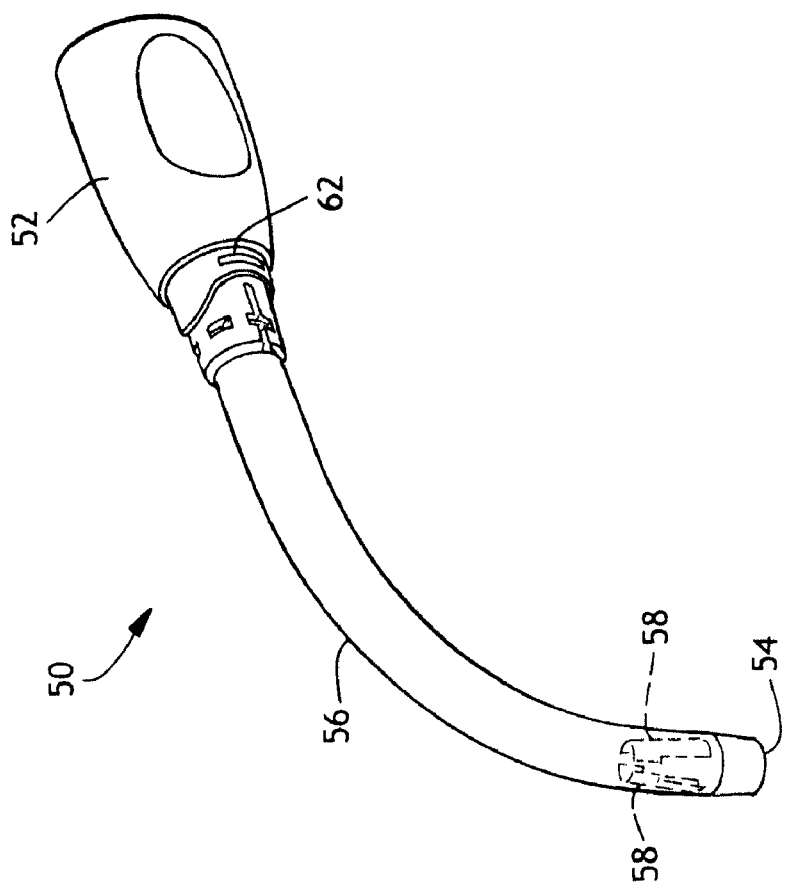
FIG. 17 is a drawing of the dilator loading catheter 50.

FIG. 17 shows the loading catheter 50. The loading catheter has a desirably freely rotating handle 52 at the proximal end and a tip 54 at the distal end. The handle 52 need not be able to rotate an entire 360 degrees but is should move sufficiently to disengage the lock mechanism used to attach the loading catheter 50 to the trach tube 26, as discussed below. The midsection 56 (between the handle 52 and tip 54) may be tubular and is flexible so that it can bend as it is inserted and removed from the trach tube 26. Suitable materials for the midsection 54 are softer plastics like polyurethanes and some polyolefins. Suitable materials for the tip 54 and handle 52 are somewhat harder plastics like nylons and some polyolefins. The device must be biocompatible, free of di(2-ethylhexyl) phthalate (DEHP) and preferably free of animal derived products.

The distal end or tip 54 has a mechanism for attaching it to the proximal end of the dilator tip 12. One type of mechanism that may be used is locking arms or snap detents 58 located within the catheter tip 54. The detents 58 can flex out and over the lock or protrusions 60 located near the proximal end 28 of the tip 12 on the inner portion 18, as shown, for example, in FIG. 6, and engage and attach the tip 12 firmly to the loading catheter 50. The mechanism for engaging the loading catheter 50 to the tip 12 may be detachable but is more desirably not detachable since a firm connection is desired to ensure that the tip 12 does not separate from the loading catheter 50 as the tip 12 is being withdrawn through the tube 26, as described in more detail below.

Figure 18:
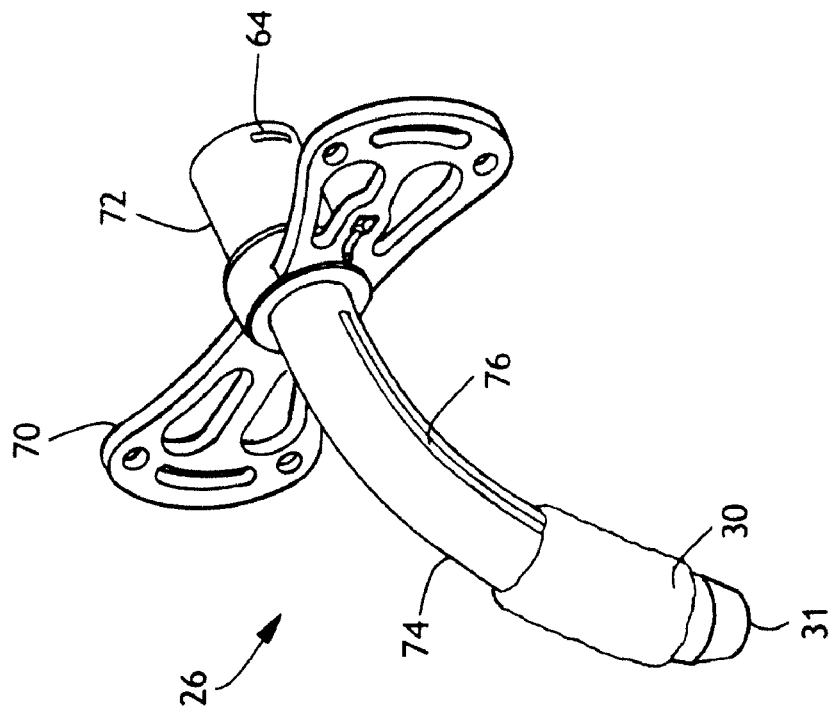
FIG. 18 is a drawing of the trachestomy tube 26.
Figure 19:
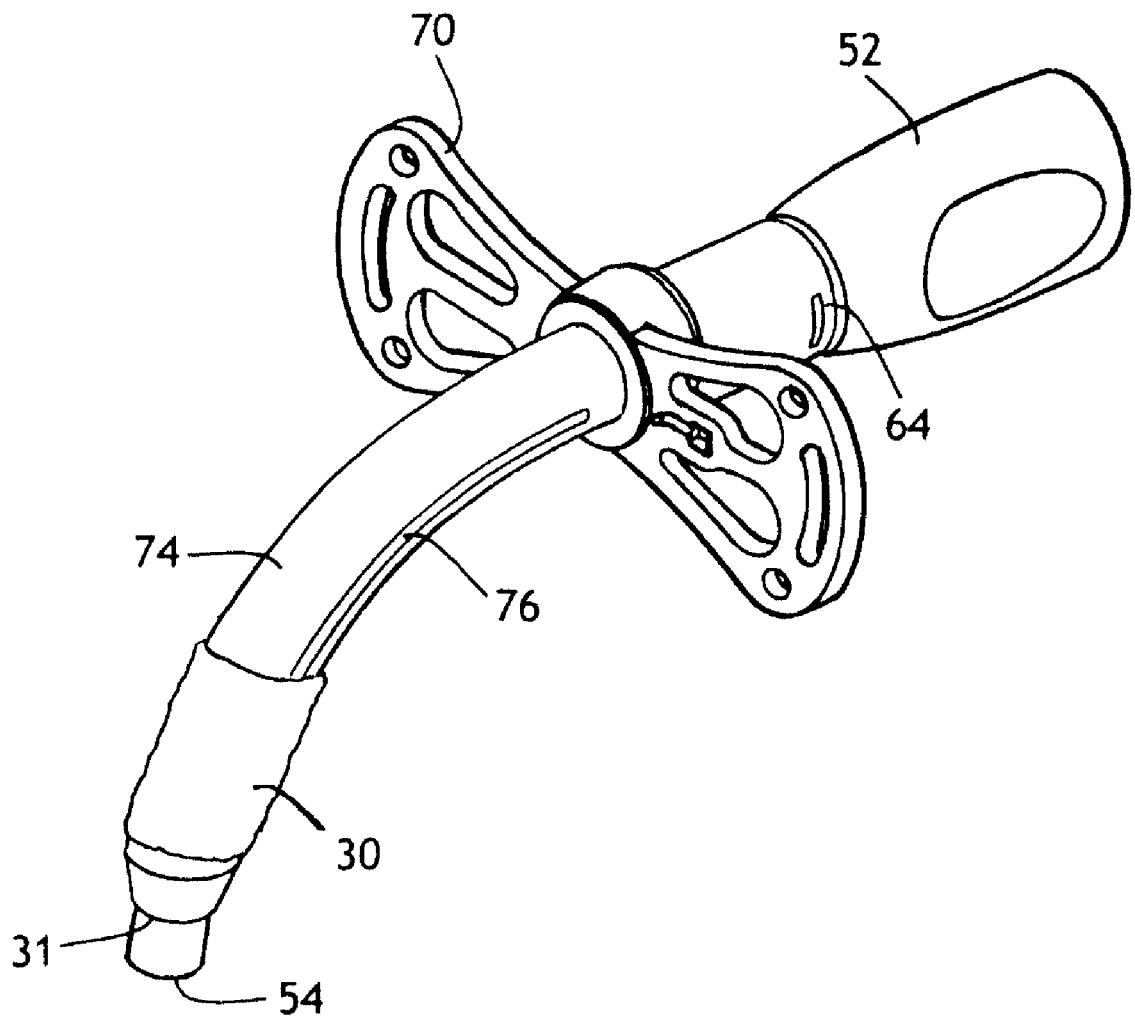
FIG. 19 is a drawing of the loading catheter 50 installed in the trach tube 26.

The tracheostomy tube is shown in FIG. 18. There is a flange 70 on the trach tube 26 on the proximal end that is used to attach the trach tube to a patient's throat. The flange 70 extends on either side of the tube 26 near the proximal end where the ventilator connection 72 is located. The flange 70 is flexible and non-irritating and can be sutured onto the throat of a patient to anchor the tube 26. The size of the flange will vary depending on the size and needs of the patient. The tube 26 also has a hollow shaft 74 extending from the proximal end to the distal end 31. An inflation line 76 runs from the proximal end to the trach tube balloon cuff 30 so that the cuff may be inflated In use, the loading catheter 50 is slid into the tracheostomy tube 26 (FIG. 19) where it remains substantially within the tube 26, with the tip 54 and handle 52 remaining outside the tube. It should be noted that the loading catheter 50 could be sized so that the tip 54 remains within the tracheostomy tube 26 if desired. The loading catheter handle 52 detachably engages the proximal end of the trach tube 26 with, for example, a slot 64 and tab 62 arrangement as shown in FIGS. 17 and 18 where there are tabs 62 on both sides of the handle 52 which mate with slots 64 on the proximal end of the trach tube 26. Those skilled in the art may easily devise alternative ways of mating the handle 52 with the tube 26.

The distance from the flange 70 to the distal tip 31 of the trach tube 26 may be an arched distance of between 70 and 100 mm, desirably between about 75 and 95 mm and more desirably between 80 and 90 mm. The angle of the trach tube from the flange to the distal end is between 85 and 120 degrees, desirably between 95 and 115 degrees, more desirably between 100 and 110 degrees. The flange 70 may desirably be of a width between 6 and 12 cm and height of 1 to 6 cm, more particularly between 7 and 10 cm and 2 and 5 cm respectively or still more particularly between 8 and 9 cm and 2 and 4 cm respectively. The loading catheter 50 has a desirably tubular midsection having a arched length between about 8 and 13 cm, particularly about 11 cm and may terminate as much as 20 mm beyond the distal tip of the trach tube or may terminate within it. The handle 52 may be between 2 and 7 cm long, particularly about 5 cm. The loading catheter distal end or tip 54 may be between 3 and 10 mm in inner diameter, particularly about 6 mm. In any event, the loading catheter midsection 56 and tip 54 and dilator tip 12 must be sized so that they will pass through the trach tube 26.

Figure 13:
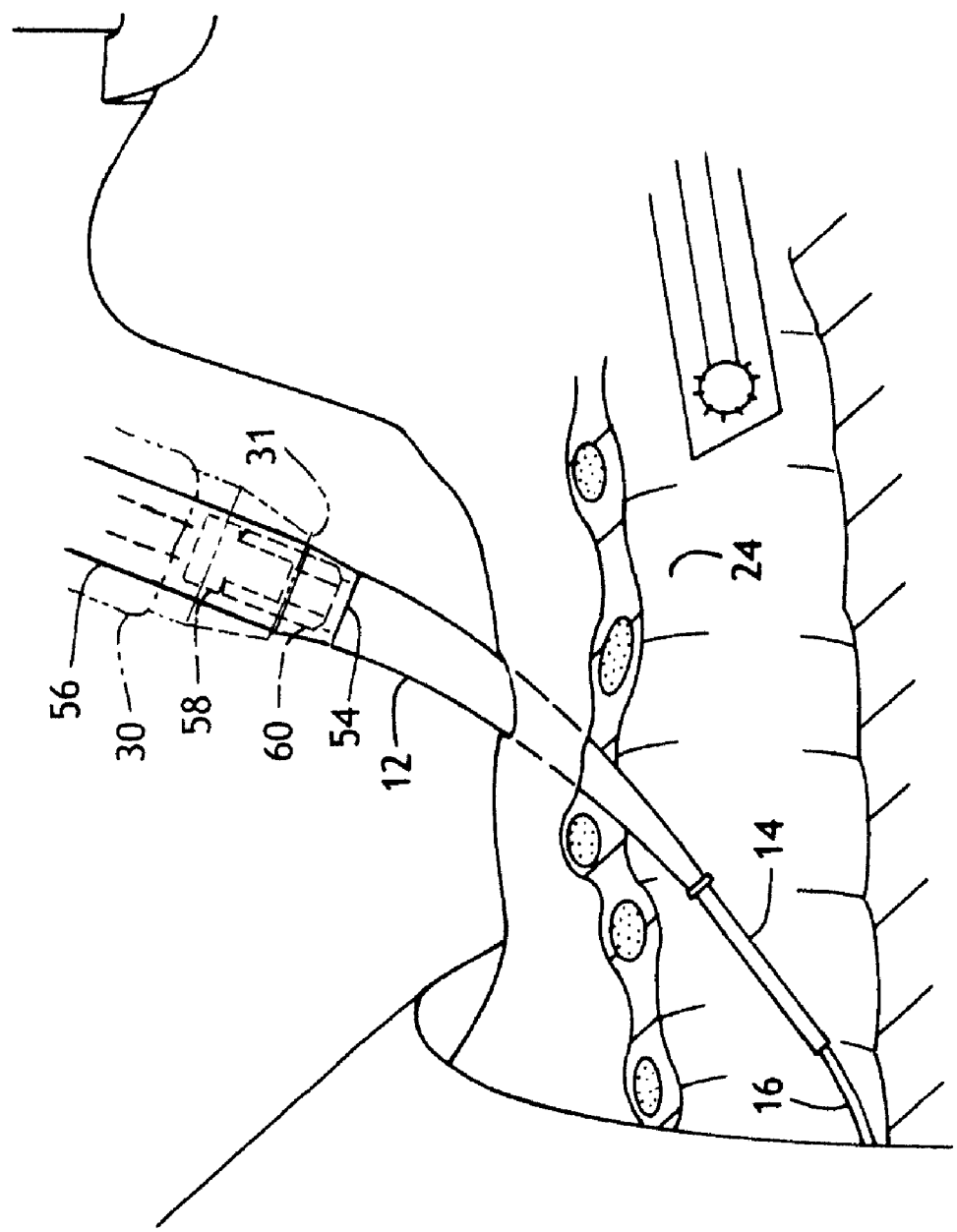
FIG. 13 is a drawing of the tracheostomy tube 26 and loading catheter 50 unit that have been passed over the inner portion of the dilator tip 12 until it reached the proximal end of the tip where the tube mates with the proximal end of the tip.
Figure 14:
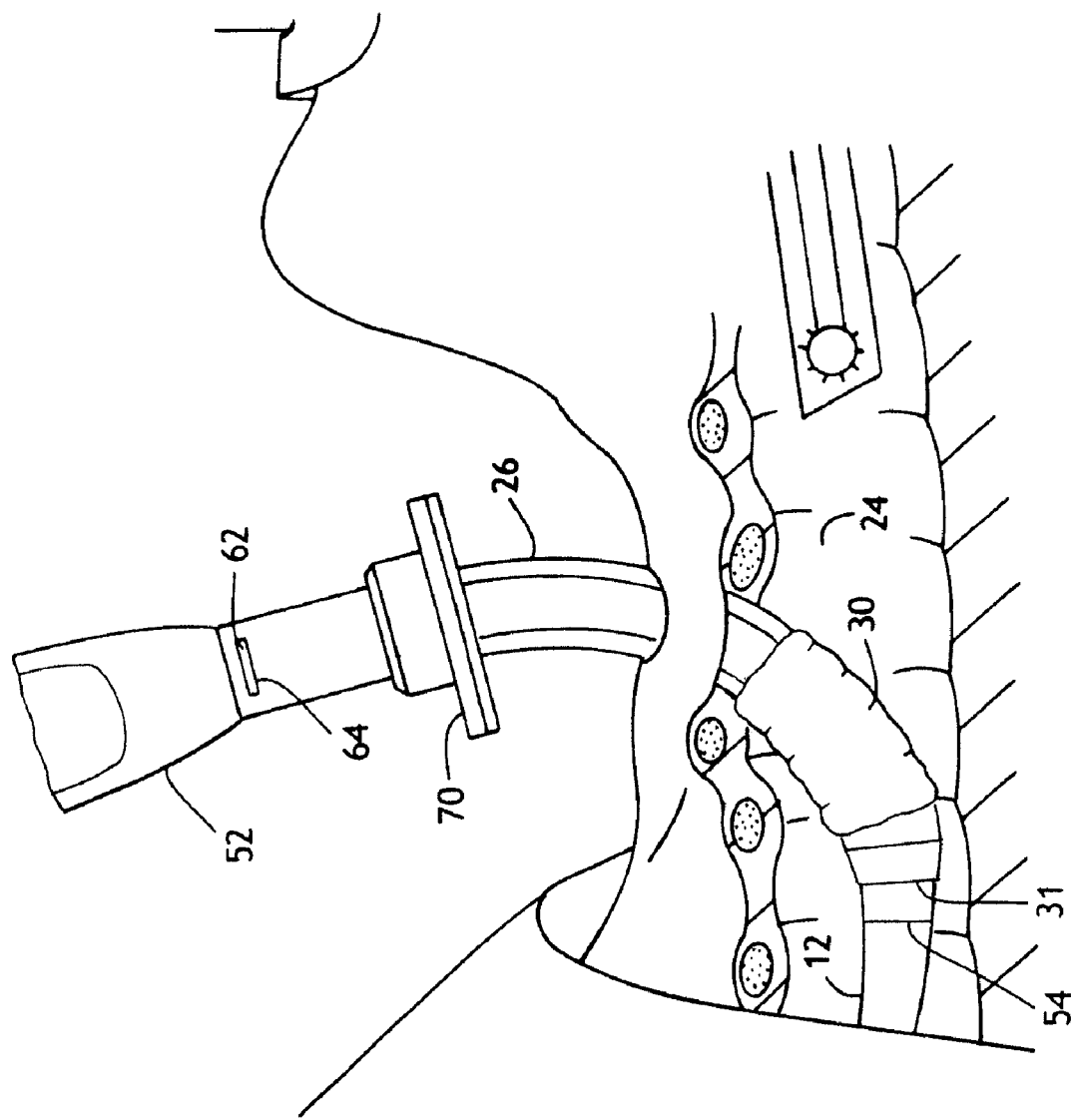
FIG. 14 is a drawing of the position of the tube and tip as they are passed into the trachea as a unit.
Figure 15:
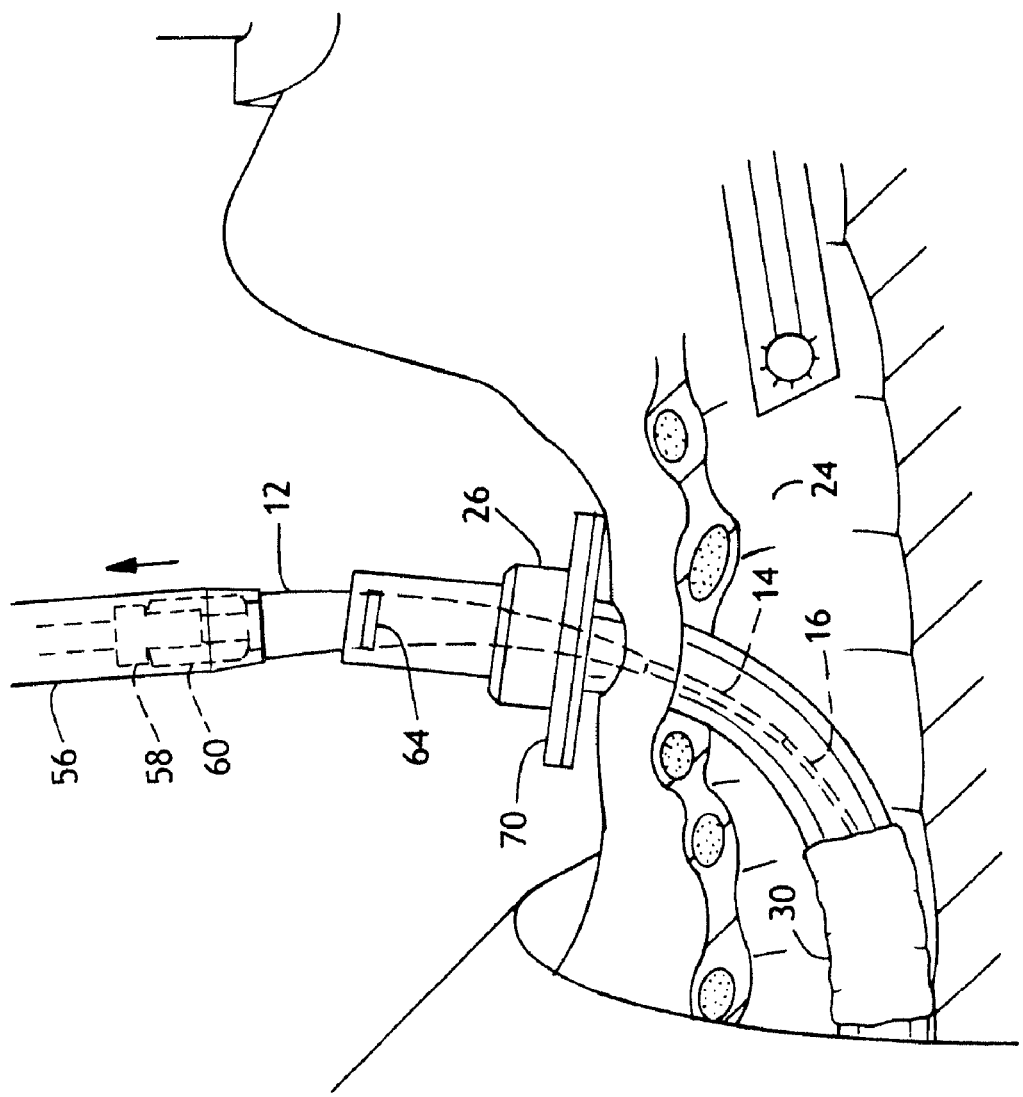
FIG. 15 is a drawing of the tip, guiding catheter and J-wire being withdrawn through the tracheostomy tube with the tube remaining in place in the trachea.
Figure 16:
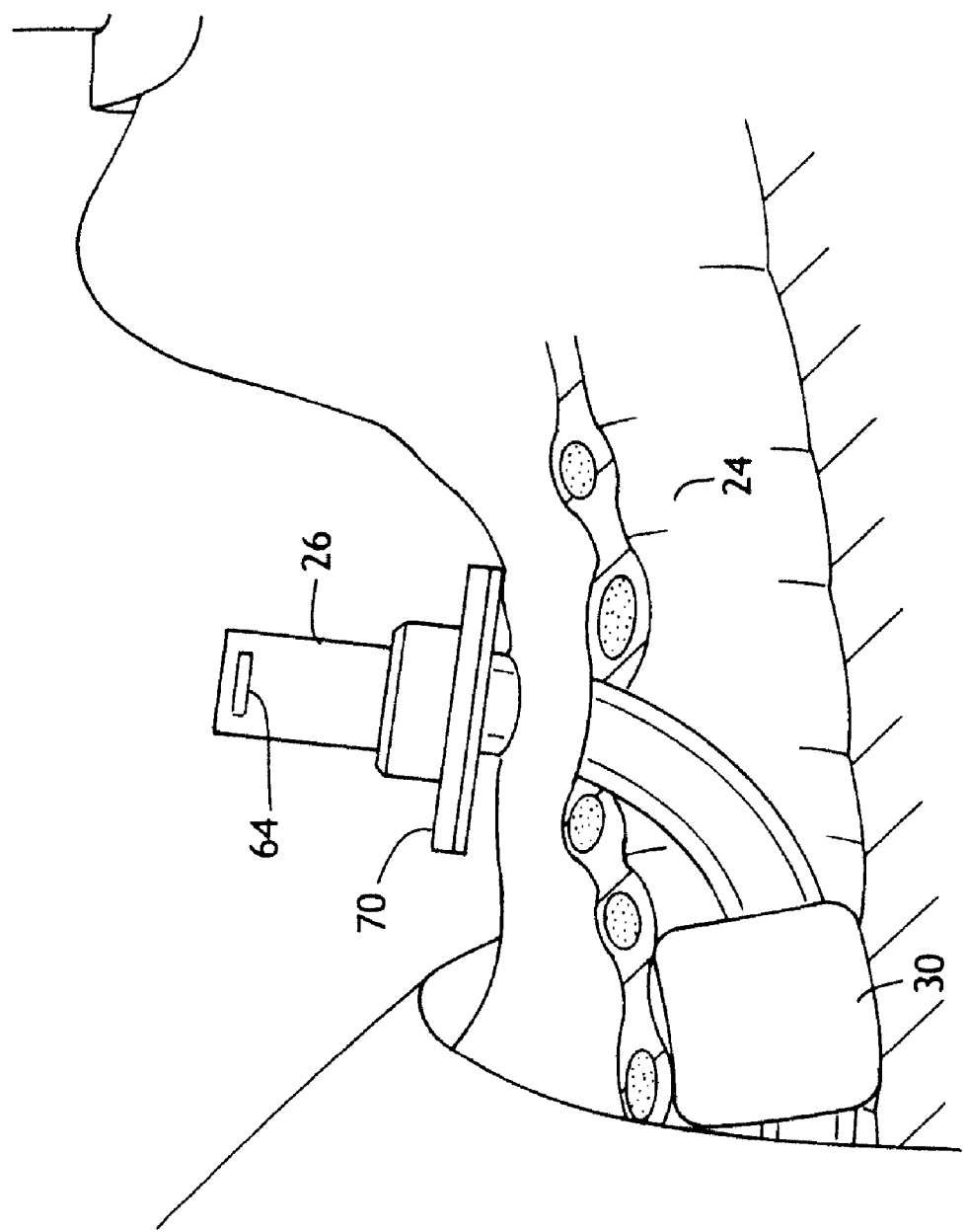
FIG. 16 is a drawing of the trach tube in its final position in the trachea, with the trach cuff inflated.

The tracheostomy tube 26 with the loading catheter 50 inserted is then passed over the inner portion 18 of the tip 12 until it reaches the proximal end 28 of the tip 12 where the distal tip 54 of the loading catheter 50 engages the proximal end 28 of the tip 12 as discussed above (FIG. 13). (Note that in FIG. 13 the trach tube is shown in phantom for ease of viewing.) The loading catheter 50, tip 12 and tube 26 are then passed into the trachea 24 as a unit (FIG. 14) to the point where the flange 70 on the tube 26 reaches the throat. Once the tube 26 is in place in the trachea 24, the loading catheter 50 with the attached tip 12, guiding catheter 14 and J-wire 16 may be withdrawn through the tracheostomy tube 26 with only the tube 26 remaining in place in the trachea 24 (FIG. 15). This may be accomplished by disengaging the detachably attached handle 52 from the proximal end of the tracheostomy tube 26 and pulling the handle 52 away from the tube 26. One way of accomplishing this disengagement is by twisting the loading catheter handle 52. This twisting action cams the loading catheter handle 52 off the proximal end of the trach tube 26, overcoming any static friction that may exist in the system and defeating the tabs 62 and slots 64 locking the loading catheter handle 52 to the tube 26. This action allows the user to pull all the loading components out through the inner lumen of the trach tube 26, leaving only the tube 26 in place. Clearly the tip 12 must be sized so that its largest diameter is slightly less than that of the tracheostomy tube 26 that it is intended to pass through. Once the trach tube 26 is in place, the tube cuff 30 is inflated and the tube 26 is connected to a ventilator (not shown) and placed in service (FIG. 16).

An optional trauma reducing feature is a lubricious coating that may be added to the tip and dilator body up to the stop ridge on the exterior and/or interior. The coating may be activated by exposure to water before the suitable dilator 10 is slipped over the guiding catheter 14. The coating may be for example, a poly(N-vinyl)lactam such as those available from Hydromer Inc., 35 Industrial Parkway, Branchburg, N.J. and as described in U.S. Pat. Nos. 5,156,601, 5,258,421, 5,420,197 and 6,054,504. The dilator may be dipped in water just before the J-wire is inserted and may be coated on the inside and/or outside. An inside coating allows the J-wire to slip through the interior of the dilator quite easily and the exterior coating avoids trauma to the skin or trachea.

Lastly, the marking line 22 at 42 French on the dilator body may instead be a an additional ridge or other marking and alternate or additional markings may be placed on the dilator body at, for example, 32, 38 or still larger French diameters.

This application is one of a group of commonly assigned patent application which are being filed on the same day. The group includes application Ser. No. 12/147,817 in the name of Brian J. Cuevas and is entitled "Easy Grip Tapered Dilator"; application Ser. No. 12/147,873 in the name of Brian J. Cuevas and is entitled "Method of Performing a Tracheostomy"; application Ser. No. 12/163,065 in the name of Brian J. Cuevas and is entitled "Dilator Loading Catheter"; application Ser. No. 12/147,952 in the name of Brian J. Cuevas and is entitled "Tracheostomy Tube Butterfly Flange"; application Ser. No. 12/163,173 in the name of James Schumacher and is entitled "Tracheostomy Tube"; design application Ser. No. 29/320,497 in the name of Brian J. Cuevas and is entitled "Butterfly Flange"; design application Ser. No. 29/320,492 in the name of Brian J. Cuevas and is entitled "Tapered Dilator Handle"; design application Ser. No. 29/320,500 in the name of Brian J. Cuevas and is entitled "Stoma Pad". The subject matter of these applications is hereby incorporated by reference.

As will be appreciated by those skilled in the art, changes and variations to the invention are considered to be within the ability of those skilled in the art. Such changes and variations are intended by the inventors to be within the scope of the invention. It is also to be understood that the scope of the present invention is not to be interpreted as limited to the specific embodiments disclosed herein, but only in accordance with the appended claims when read in light of the foregoing disclosure.

What is claimed is:

1. A method of performing a tracheostomy comprising the steps of:
   introducing a dilator having at least a tip detachably attached to a body, into an opening in a trachea of a patient,
   dilating said trachea with said dilator,
   partially removing said dilator from the trachea, leaving said dilator tip partially into the trachea,
   removing said detachable body from said dilator tip,
   mating a loading catheter with the tip, wherein said loading catheter is substantially within a tracheostomy tube,
   passing said tip, loading catheter and tracheostomy tube into said trachea,
   removing said loading catheter and said tip from said trachea through said tracheostomy tube.

2. The method of claim 1 further wherein said dilator comprises a locking means to hold the tip in place within the body prior to removal of the body.

3. The method of claim 2 wherein said locking means is a slot located on the proximal end of the body and a flange on an inner portion of the tip.

4. The method of claim 1 further comprising aligning said dilator using a guiding line running length-wise on an uppermost surface of said dilator.

* * * * *